(12) United States Patent
Oakey et al.

(10) Patent No.: US 7,318,902 B2
(45) Date of Patent: Jan. 15, 2008

(54) LAMINAR FLOW-BASED SEPARATIONS OF COLLOIDAL AND CELLULAR PARTICLES

(75) Inventors: John Oakey, Golden, CO (US); David W. M. Marr, Golden, CO (US)

(73) Assignee: Colorado School of Mines, Golden, CO (US)

( * ) Notice: Subject to any disclaimer, the term of this patent is extended or adjusted under 35 U.S.C. 154(b) by 70 days.

(21) Appl. No.: 10/248,653

(22) Filed: Feb. 4, 2003

(65) Prior Publication Data

US 2003/0159999 A1 Aug. 28, 2003

Related U.S. Application Data

(60) Provisional application No. 60/354,372, filed on Feb. 4, 2002.

(51) Int. Cl.
*B01D 37/00* (2006.01)
*B01D 57/00* (2006.01)

(52) U.S. Cl. .................. 210/767; 210/695; 366/336; 422/101; 422/186.1

(58) Field of Classification Search ........... 204/450, 204/451, 453, 600, 601, 603; 210/222, 223, 210/243, 695, 748, 767; 366/336; 422/50, 422/101, 186.1, 186.01, 186.03; 436/180, 436/514, 518, 526; 435/173.1
See application file for complete search history.

(56) References Cited

U.S. PATENT DOCUMENTS 4,190,535 A 2/1980 Luderer
5,304,487 A 4/1994 Wilding et al.
5,427,663 A 6/1995 Austin (Continued)

FOREIGN PATENT DOCUMENTS

DE 19712309 A1 5/1998

(Continued)

OTHER PUBLICATIONS

S. Takayama, J. Cooper McDonald, E. Ostuni, M.N. Liang, P.J.A. Kenis, R.F. Ismagilov and G.M. Whitesides, "Patterning Cells and Their Environments Using Multiple Laminar Fluid Flows in Capillary Networks", *Proceedings of the National Academy of Sciences of the United States of America*, May 11, 1999, pp. 5545-5548, 96-#10, National Academy of Sciences, USA.

(Continued)

*Primary Examiner*—David A. Reifsnyder
(74) *Attorney, Agent, or Firm*—Sheridan Ross P.C.

(57) ABSTRACT

A system, method and apparatus employing the laminar nature of fluid flows in microfluidic flow devices in separating, sorting or filtering colloidal and/or cellular particles from a suspension in a microfluidic flow device is disclosed. The microfluidic flow device provides for separating a particle within a suspension flow in a microfluidic flow chamber. The chamber includes a microfluidic channel comprising at least one inlet port for receiving a suspension flow under laminar conditions, a first outlet port and a second outlet port. The chamber further includes an interface for translating a particle within the channel. The first outlet port receives a first portion of the suspension exiting the said channel and the second outlet port receives the particle in a second portion of the suspension exiting the channel.

11 Claims, 12 Drawing Sheets

U.S. PATENT DOCUMENTS

| | | | |
|---|---|---|---|
| 5,541,072 A | 7/1996 | Wang et al. | |
| 5,622,831 A | 4/1997 | Liberti et al. | |
| 5,639,669 A | 6/1997 | Ledley | |
| 5,707,799 A | 1/1998 | Hansmann et al. | |
| 5,715,946 A | 2/1998 | Reichenbach | |
| 5,750,339 A | 5/1998 | Smith | |
| 5,770,029 A | 6/1998 | Nelson et al. | |
| 5,837,115 A | 11/1998 | Austin | |
| 5,858,188 A | 1/1999 | Soane et al. | |
| 5,866,345 A | 2/1999 | Wilding et al. | |
| 5,928,880 A | 7/1999 | Wilding et al. | |
| 5,952,173 A | 9/1999 | Hansmann et al. | |
| 6,007,690 A | 12/1999 | Nelson | |
| 6,054,034 A | 4/2000 | Soane et al. | |
| 6,074,827 A | 6/2000 | Nelson | |
| 6,156,270 A | 12/2000 | Buechler | |
| 6,197,523 B1 | 3/2001 | Rimm et al. | |
| 6,221,671 B1 | 4/2001 | Groner et al. | 436/63 |
| 6,241,894 B1 | 6/2001 | Briggs et al. | |
| 6,251,691 B1 | 6/2001 | Seul | |
| 6,256,093 B1 | 7/2001 | Johnson | 356/335 |
| 6,265,229 B1 | 7/2001 | Fodstad et al. | |
| 6,315,940 B1 | 11/2001 | Nisch et al. | |
| 6,344,326 B1 | 2/2002 | Nelson | |
| 6,361,958 B1 | 3/2002 | Shieh | |
| 6,368,871 B1* | 4/2002 | Christel et al. | 366/336 |
| 6,387,290 B1 | 5/2002 | Brody et al. | |
| 6,432,630 B1* | 8/2002 | Blankenstein | 422/186.1 |
| 6,454,938 B2 | 9/2002 | Moon et al. | |
| 6,465,225 B1* | 10/2002 | Fuhr et al. | 210/695 |
| 6,540,895 B1 | 4/2003 | Spence et al. | |
| 6,613,525 B2 | 9/2003 | Nelson et al. | |
| 6,632,619 B1 | 10/2003 | Harrison et al. | |
| 6,635,163 B1 | 10/2003 | Han et al. | |
| 6,664,104 B2 | 11/2003 | Pourahmadi et al. | |
| 6,685,841 B2 | 2/2004 | Lopez et al. | |
| 6,746,503 B1 | 6/2004 | Benett et al. | |
| 6,762,059 B2 | 7/2004 | Chan et al. | |
| 6,783,647 B2 | 8/2004 | Culbertson et al. | |
| 6,815,664 B2* | 11/2004 | Wang et al. | 435/173.1 |
| 6,878,271 B2 | 4/2005 | Gilbert et al. | |
| 6,881,315 B2 | 4/2005 | Iida et al. | |
| 6,893,881 B1 | 5/2005 | Fodstad et al. | |
| 6,913,697 B2 | 7/2005 | Lopez et al. | |
| 6,958,245 B2 | 10/2005 | Seul et al. | |
| 2001/0036672 A1 | 11/2001 | Anderson et al. | |
| 2002/0005354 A1 | 1/2002 | Spence et al. | |
| 2002/0058332 A1* | 5/2002 | Quake et al. | 422/101 |
| 2002/0090741 A1 | 7/2002 | Jurgensen et al. | |
| 2002/0108859 A1 | 8/2002 | Wang et al. | |
| 2002/0113204 A1 | 8/2002 | Wang et al. | |
| 2002/0115163 A1 | 8/2002 | Wang et al. | |
| 2002/0115164 A1 | 8/2002 | Wang et al. | |
| 2002/0123078 A1 | 9/2002 | Seul et al. | |
| 2002/0123112 A1 | 9/2002 | Wang et al. | |
| 2002/0132315 A1 | 9/2002 | Wang et al. | |
| 2002/0132316 A1 | 9/2002 | Wang et al. | |
| 2002/0172987 A1 | 11/2002 | Terstappen et al. | |
| 2003/0072682 A1 | 4/2003 | Kikinis | |
| 2003/0077292 A1 | 4/2003 | Hanash et al. | |
| 2004/0018116 A1 | 1/2004 | Desmond et al. | |
| 2004/0072278 A1 | 4/2004 | Chou et al. | |
| 2004/0121343 A1 | 6/2004 | Buechler et al. | |
| 2004/0144651 A1 | 7/2004 | Huang et al. | |
| 2005/0049793 A1 | 3/2005 | Paterlini-Brechot | |
| 2005/0164158 A1 | 7/2005 | Wang et al. | |
| 2006/0060767 A1 | 3/2006 | Wang et al. | |

FOREIGN PATENT DOCUMENTS

| | | |
|---|---|---|
| EP | 1221342 A2 | 7/2002 |
| EP | 1412729 A2 | 1/2003 |
| EP | 1438398 A2 | 5/2003 |
| EP | 1338894 A2 | 8/2003 |
| EP | 1485713 A1 | 9/2003 |
| EP | 1499706 A2 | 10/2003 |
| EP | 1539350 A1 | 1/2004 |
| EP | 1529211 A1 | 2/2004 |
| EP | 1542802 A1 | 3/2004 |
| EP | 1418003 A1 | 5/2004 |
| EP | 1462800 A1 | 9/2004 |
| WO | WO94/29707 | 12/1994 |
| WO | WO-98/10267 A1 | 3/1998 |
| WO | WO99/44064 A1 | 9/1999 |
| WO | WO 00/00816 A1 * | 1/2000 |
| WO | WO 02/12896 A1 | 2/2002 |
| WO | WO 02/28523 A2 | 4/2002 |
| WO | WO 02/30562 A1 | 4/2002 |
| WO | WO 02/44689 | 6/2002 |
| WO | WO 03/031938 A3 | 4/2003 |
| WO | WO 2004/029221 | 4/2004 |
| WO | WO 2004/037374 | 5/2004 |
| WO | WO 2004/056978 A1 | 7/2004 |

OTHER PUBLICATIONS

P.J.A. Kenis, R.F. Ismagilov and G.M. Whitesides, "Microfabrication Inside Capillaries Using Multiphase Laminar Flow Patterning", *Science*, Jul. 2, 1999, pp. 83-85, 285, American Association for the Advancement of Science, USA.

N.L. Jeon, S.K.W. Dertinger, D.T. Chiu, I.S. Choi, A.D. Stroock and G.M. Whitesides, "Generation of Solution and Surface Gradients Using Microfluidic Systems", *Langmuir*, 2000, pp. 8311-8316, 16-#22, American Chemical Society, USA.

B.H Weigl and P. Yager, "Microfluidic Diffusion-Based Separation and Detection", *Science*, Jan. 15, 1999, pp. 346-347, 283-#5400, American Association for the Advancement of Science, USA.

P.C H. Li and D.J. Harrison, "Transport, Manipulation, and Reaction of Biological Cells On-Chip Using Electrokinetic Effects", *Analytical Chemistry*, Apr. 15, 1997, pp. 1564-1568, 69-#8, American Chemical Society, USA.

S. Fiedler, S.G. Shirley, T. Schnelle and G. Fuhr, "Dielectrophoretic Sorting of Particles and Cells in a Microsystem", *Analytical Chemistry*, May 1, 1998, pp. 1909-1915, 70-#9, American Chemical Society, USA.

A.Y. Fu, C. Spence, A. Scherer, F.H. Arnold and S.R. Quake, "A Microfabricated Flourescence-Activated Cell Sorter", *Nature Biotechnology*, Nov. 1999, pp. 1109-1111, 17, Nature America Inc., USA.

Y. Huang, K.L. Ewalt, M. Tirado, R. Haigis, A. Forster, D. Ackley, M.J. Heller, J.P. O'Connell and M. Krihak, "Electric Manipulation of Bioparticles and Macromolecules on Microfabricated Electrodes", *Analytical Chemistry*, Apr. 1, 2001, pp. 1549-1559, 73-#7, American Chemical Society, USA.

S. Takayama, E. Ostuni, P. Leduc, K. Naruse, D.E. Ingber and G. M. Whitesides, "Subcellular Position of Small Molecules", *Nature*, Jun. 28, 2001, p. 1016, 411, Nature Publishing Group (USA), a division of Macmillan Publishers Ltd., United Kingdom.

G. Fuhr and S.G. Shirley, "Biological Application of Microstructures", *Topics in Current Chemistry*, 1997, pp. 83-116, 194, Springer-Verlag, Germany.

A.E. Kamholz, B.H. Weigl, B.A. Finlayson and P. Yager, "Quantitative Analysis of Molecular Interaction in a Microfluidic Channel: the T-Sensor", *Analytical Chemistry*, Dec. 1, 1999, pp. 5340-5347, 71-#23, American Chemical Society, USA.

M. Eigen and R. Rigler, "Sorting Single Molecules: Application to Diagnostics and Evolutionary Biotechnology", *Proceedings of the National Academy of Sciences of the United States of America*, Jun. 1994, pp. 5740-5747, 91, National Academy of Sciences, USA.

C.F. Chou, O. Bakajin, S.W. P. Turner, T. Duke, S.S. Chan, E.C. Cox, H.G. Craighead and R.H. Austin, "Sorting by Diffusion: an Asymmetric Obstacle Course for Continuous Molecular Separation", *Proceedings of the National Academy of Sciences of the*

*United Sates of America*, Nov. 23, 1999, pp. 13762-13765, 96-#24, National Academy of Sciences, USA.

H.P. Chou, C. Spence, A. Scherer and S. Quake, "A Microfabricated Device for Sizing and Sorting DNA Molecules", *Proceedings of the National Academy of Sciences of the United States of America*, Jan. 5, 1999, pp. 11-13, 96-#1, National Academy of Sciences, USA.

E. Delamarche, A. Bernard, H. Schmid, A. Bietsch. B. Michel and H. Biebuyck, "Microfluidic Networks for Chemical Patterning of Substrates: Design and Application to Bioassays", *Journal of the American Chemical Society*, Jan. 9, 1998, pp. 500-508, 120, American Chemical Society, USA.

E. Delamarche, A. Bernard, H. Schmid, B. Michel and H. Biebuyck, "Patterned Delivery of Immunoglobulins to Surfaces Using Microfluidic Networks", *Science*, May 2, 1997, pp. 779-781, 276, American Association for the Advancement of Science, USA.

D.T. Chiu, N.L. Jeon, S. Huang, R.S. Kane, C.J. Wargo, I.S. Choi, D.E. Ingber and G.M. Whitesides, "Patterned Deposition of Cells and Proteins Onto Surfaces by Using Three-Dimensional Microfluidic Systems", *Proceedings of the National Academy of Sciences of the United States of America*, Mar. 14, 2000, pp. 2408-2413, 97-#6, National Academy of Sciences, USA.

A.Y. Fu, H.P. Chou, C. Spence, F.H. Arnold and S.R. Quake, "An Integrated Microfabricated Cell Sorter", *Analytical Chemistry*, Jun. 1, 2002, pp. 2451-2457, 74-#11, American Chemical Society, USA.

M. Freemantle, "Downsizing Chemistry", *Chemical & Engineering News*, Feb. 22, 1999, pp. 27-36, 77-#8, American Chemical Society, USA.

D.J. Beebe, J.S. Moore, J. M. Bauer, Q. Yu, R. H. Liu, C. Devadoss and B.Y. Jo, "Functional Hydrogel Structures for Autonomous Flow Control Inside Microfluidic Channels", *Nature*, Apr. 6, 2000, pp. 588-590, 404, Nature Publishing Group (USA), a division of Macmillan Publishers Ltd., United Kingdom.

J. Oakey, J. Allely and D.W.M. Marr, "Laminar Flow-Based Separations at the Microscale", *Biotechnology Progress*, Sep. 24, 2002, pp. 1439-1442, 18-#6, American Chemical Society and the American Institute of Chemical Engineers, USA.

R.J. Olson, H.M. Sosik and A.J. Williams III, "An In Situ Flow Cytometer for the Optical Analysis of Individual Particles in Seawater", found at http://www.whoi.edu/science/B/Olsonlab/insitu2001.htm, publication date unknown.

Product literature for GEM, a system for blood testing: "GEM PCL Step by Step Guide" and "GEM Premier 3000", publication date unknown.

Archer et al. Cell Reactions to Dielectrophoretic Manipulation. *Biochemical and Biophysical Research Communications*. 1999;257:687-98.

Ashcroft, Neil W., Mermin, David N. Solid State Physics. Orlando, FL: Saunders College Publishing; 1976.

Bauer, J. Advances in cell separation: recent developments in counterflow centrifugal elutriation and continuous flow cell separation. *Journal of Chromatography*. 1999:722:55-69.

Becker et al. Fabrication of Microstructures With High Aspect ratios and Great Structural Heights by Synchrotron Radiation Lithography, Galvanoforming, and Plastic Moulding (LIGA Process). *Microelectronic Engineering*. 1986;4:35-56.

Becker et al. Planar quartz chips with submicron channels for two-dimensional capillary electrophoresis applications. *J. Micromech Microeng*.1998;9:24-28.

Benincasa et al. Cell Sorting by One Gravity SPLITT Fractionation. *Analytical Chemistry*. 2005; 77(16):5294-5301.

Berg HC. Random Walks in Biology. *Princeton University Press*. Princeton, NJ; 1983.

Chou et al. Sorting by diffusion: An asymmetric obstacle course for continuous molecular separation. *PNAS*. 1999; 96(24):13762-13765.

de Kretser et al. The Separation of Cell Populations using Monoclonal Antibodies attached to Sepharose. *Tissue Antigens*. 1980;16:317-325.

Deshmukh et al. Continuous Micromixer With Pulsatile Micropumps. *Solid-State Sensor and Actuator Workshop*. Hilton Head Island, South Carolina; Jun. 4-8, 2000:73-76.

Evans et al. The Bubble Spring and Channel (BSAC) Valve: An Actuated, Bi-Stable Mechanical Valve For In-Plane Fluid Control. *Transducers '99*. Sendai, Japan; Jun. 7-10, 1999.

Farooqui et al. Microfabrication of Submicron Nozzles in Silicon Nitride. *Journal of Microelectromechanical Systems*. 1992; 1(2):86-88.

Fu et al. An integrated miscrofabricated cell sorter. *Analytical Chemistry*. 2002;74(11):2451-2457.

Giddings, J.C. Unified Separation Science. John Wiley & Sons, Inc. 1991; Cover Page & Table of Contents only.

Giddings, J. C. Chemistry 'Eddy' Diffusion in Chromatography. *Nature*. 1959;184:357-358.

Giddings, J. C. Field-Flow Fractionation: Analysis of Macromolecular, Colloidal, and Particulate Materials. *Science*. 1993;260:1456-1465.

Han et al. Separation of Long DNA Molecules in a Microfabricated Entropic Trap Array. *Science*. 2000;288: 1026-1029.

Huang et al. A DNA prism for high-speed continuous fractionation of large DNA molecules. *Nature Biotecnology*. 2002;20: 1048-1051.

Huang et al. Role of Molecular Size in Ratchet Fractionation. 2002; 89(17): 178301-1-178301-4.

Huh et al. Gravity-driven microhydrodynamics-based cell sorter (microHYCS) for rapid, inexpensive, and efficient cell separation and size-profiling. *2nd Annual International IEEE-EMBS Special Topic Conference on Microtechnology in Medicine and Biology*. Madison, Wisconsin USA; May 2-4, 2002:466-469.

Kim et al. Polymer microstructures formed by moulding in capillaries. *Nature*. 1995;376:581-584.

Kumar et al. Cell Separation: A Review. *Pathology*. 1984;16:53-62.

Mehrish et al. Electrophoresis of cells and the biological relevance of surface charge. *Electrophoresis*. 2002;23:1984-1994.

Moore et al. Lymphocyte fractionation using immunomagnetic colloid and a dipole magnet flow cell sorter. *J Biochem Biophys Methods*. 1998;37:11-33.

Raymond et al. Continuous Separation of High Molecular Weight Compounds Using a Microliter Volume Free-Flow Electrophoresis Microstructure. 1996;68:2515-2522.

Tong et al. Low Temperature Wafer Direct Bonding. *Journal of Microelectromechanical Systems*. 1994;3:29-35.

Turner et al. Confinement-Induced Entropic Recoil of Single DNA Molecules in a Nanofluidic Structure. *Physical Review Letters*. 2002;88:128103.1-128103.4.

Voldman et al. Holding Forces of Single-Particle Dielectrophoretic Traps. *Biophysical Journal*.2001;80:531-541.

Volkmuth et al. DNA electrophoresis in microlithographic arrays. Letters to Nature (1992) vol. 358; p. 600.

Xu et al. Dielectrophoresis of human red cells in microchips. *Electrophoresis*. 1999;20:1829-1831.

Zhang et al. High-speed free-flow electrophoresis on chip. *Anal Chem*. 2003;75:5759-5766.

\* cited by examiner

LAMINAR FLOW-BASED SEPARATIONS OF COLLOIDAL AND CELLULAR PARTICLES

CROSS REFERENCE TO RELATED APPLICATIONS

This application claims the priority benefit of U.S. Provisional Patent Application Serial No. 60/354,372 filed on Feb. 4, 2002 is herein incorporated in its entirety.

FIELD OF THE INVENTION

The present invention relates to a general class of devices that uniquely employ laminar flows in separating, filtering or sorting colloidal or cellular particles from a suspension within microfluidic devices.

BACKGROUND OF THE INVENTION

Microfluidic flows are particularly useful due to their ultra laminar nature that allows for highly precise spatial control over fluids, and provides both unique transport properties and the capability for parallelization and high throughput. These qualities have made microfluidic platforms a successful option for applications in printing, surface patterning, genetic analysis, molecular separations and sensors. Specifically, the effective separation and manipulation of colloidal and cellular suspensions on the microscale has been pursued with keen interest due to the tremendous multidisciplinary potential associated with the ability to study the behavior of individual particles and cells. Devices that employ electric fields to direct flow for the purpose of sorting and manipulating populations of cells have been realized and in some cases have demonstrated potential to achieve efficiencies comparable to their conventional analog, fluorescent activated cell sorters (FACS).

SUMMARY OF THE INVENTION

The present invention relates to a system, method and apparatus employing the laminar nature of fluid flows in microfluidic flow devices in separating, sorting or filtering colloidal and/or cellular particles from a suspension in a microfluidic flow device. In one embodiment, a microfluidic flow device is provided for separating a particle within a suspension flow in a microfluidic flow chamber. The chamber includes a microfluidic channel comprising an inlet port for receiving a suspension flow under laminar conditions, a first outlet port and a second outlet port. The chamber further includes an interface for translating a particle within the channel. The first outlet port receives a first portion of the suspension exiting the channel and the second outlet port receives the particle in a second portion of the suspension exiting the channel.

An alternative microfluidic flow device for separating a particle from a suspension flow into a second fluid flow is also provided. The microfluidic flow device includes a microfluidic channel comprising a first inlet port for receiving the suspension flow, a second inlet port for receiving the second fluid flow, a first outlet port and a second outlet port. The channel is adapted to receive the suspension flow and the second fluid flow under laminar conditions. The device further includes an interface for translating a particle from the suspension flow to the second fluid flow. The first outlet port is adapted to receive at least a portion of the suspension flow exiting the channel and the second outlet port is adapted to receive the particle in at least a portion of the second fluid flow exiting channel.

A method of separating a particle within a suspension is also provided in which a suspension flow is received in a microfluidic channel under laminar conditions. A particle in the suspension is translated within the suspension flow. A first portion of the suspension flow exits through a first outlet port, and the particle exits in a second portion of the suspension flow through a second outlet port.

Another method of separating a particle from a suspension flow is provided in which a suspension flow and a second fluid flow are received in a microfluidic channel. The suspension and the second fluid flow under laminar conditions in the channel. A particle is separated from the suspension flow into the second fluid flow. At least a portion of the suspension flow exits through a first outlet port, and the particle exits in at least a portion of the second fluid flow through a second outlet port.

A cartridge is also provided for use in system to separate a particle from a suspension flow. The cartridge comprises a microfluidic channel including an inlet port for receiving a suspension flow under laminar conditions, a first outlet port and a second outlet port. The cartridge further comprises an interconnect for connecting the cartridge to the system. The microfluidic channel is adapted to receive the suspension flow and provide an environment for translating the particle within the suspension flow. The first outlet port is adapted to receive a first portion of the suspension flow, and the second outlet port is adapted to receive the particle in a second portion of the suspension flow.

An alternative cartridge is further provided for use in system to separate a particle from a suspension flow into a second fluid flow. The cartridge comprises a microfluidic channel including a first inlet port for receiving the suspension flow, a second inlet port for receiving the second fluid flow, a first outlet port and a second outlet port. The channel is further adapted to receive the suspension flow and the second fluid flow in the channel under laminar conditions. The cartridge further comprises an interconnect for connecting the cartridge to the system. The microfluidic channel is adapted to provide an environment for translating the particle from the suspension flow to the second fluid flow. The first outlet port is adapted to receive at least a portion of the suspension flow, and the second outlet port is adapted to receive the particle in at least a portion of the second fluid flow.

A system for separating a particle from a solution in a microfluidic flow device is also provided. The system includes a detector, an information processor and an actuator. The detector monitors a microfluidic channel of the microfluidic flow device and provides an output to the information processor. The information processor processes the output to determine if the particle is present. If the particle is present, the information processor triggers the actuator to translate the particle within the channel.

A microfluidic chemical dispenser for dispensing a fluid flow into a plurality of receptacles is further provided. The dispenser comprises a first inlet port, a second inlet port, a third inlet port, a central channel, a plurality of outlet ports, and a modulator. The channel is adapted to receive, under laminar conditions, a first fluid flow through the first input port, a second fluid flow through the second input port and a third fluid flow through the third input port. The second input port is positioned at a first angle to the first input port, and the third input port is positioned at a second angle to the first input port. The modulator modulates the flow rates of the second and third fluid flows to dispense the first fluid flow into a plurality of outlet ports.

The foregoing and other features, utilities and advantages of the invention will be apparent from the following more particular description of a preferred embodiment of the invention as illustrated in the accompanying drawings.

DETAILED DESCRIPTION

The processes and devices described herein relate to actuated or non-actuated separation of various colloidal and/or cellular particles from a suspension flowing under laminar conditions in a microfluidic flow device. The colloidal and cellular particles may include, for example, polymeric, inorganic or other abiotic colloidal particles, individual polymers, proteins, fragments of DNA or RNA, entire sections or genomes of DNA, cells including single-celled organisms, formed bodies such as they would appear in blood, viruses and the like. A microfluidic flow device, as used for the purposes of the present invention, refers to a microscale device that handles volumes of liquid on the order of nanoliters or picoliters.

Under "laminar" flow conditions, a fluid flows through a channel without turbulence. The quantification of laminar or nonturbulent behavior is typically done through calculation of the Reynolds number, $Re=\rho v D/\eta$, where $\rho$ is the fluid density, $\eta$ is the fluid viscosity, $v$ is the fluid velocity, and $D$ is some characteristic channel dimension (typically the channel width). If the Reynolds number is small (<1000) for typical channel geometries, then flow is laminar, reversible, and non-turbulent. For this reason, the diameter of the channel can be designed to account for the intended fluid properties and fluid velocity, or, equivalently, the fluid velocity can be determined by the fluid properties and the channel diameter.

Figure 1:
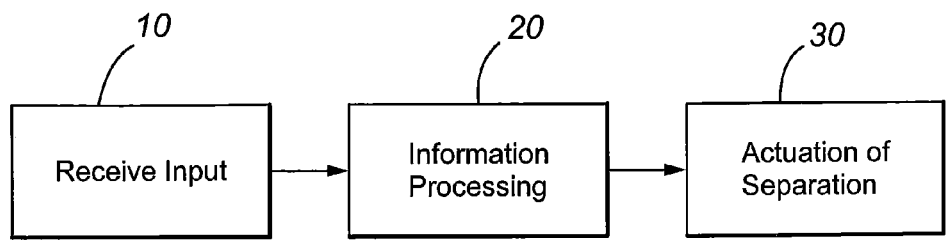
FIG. 1 depicts a flow diagram of an actuated process of separating a colloidal or cellular particle from a suspension in a microfluidic flow device.

FIG. 1 shows a flow diagram of a process for an actuated separation of colloidal and/or cellular particles from a suspension flowing through a microfluidic flow device under laminar conditions. In the receive input block 10, an input is received from a sensor monitoring a target region for a particle of interest. The target region may be monitored to detect any known attribute (or absence thereof) that can be used to distinguish a particle from the remaining suspension. An imaging device such as a charge-coupled device (CCD) camera, for example, may be utilized to capture a stream of images that may be used to identify a particle by its particular morphological attributes or motility. Alternatively, signatures, fingerprints or indices such as a fluorescent signature, light scattering signature, optical fingerprint, X-ray diffraction signature or index of refraction, and the like, or any combination of these, may be used to distinguish the particle from the remaining suspension. Surface charges of particles may also be used to distinguish the particle by observing the reaction of the particle to an applied electric or magnetic field.

Further, the suspension or the individual particles may be pretreated, as known in the art, to enhance the recognition of the particles. The suspension may further be pretreated with an antibody that will bind specifically to a particular type of particle may be used to enable or enhance the recognition of the particle. A suspension of cells, for example, may be pretreated with antibody-decorated magnetic particles and passed through a magnetic field to distinguish the particles from the remaining suspension. Similarly, other recognition methodologies known in the art may be used to distinguish the particle of interest from the remaining suspension.

Information processing block 20 performs any processing steps necessary to distinguish the particle from the remaining suspension such as comparing received images or signals from the receive input block 10 to threshold values, e.g., size and shape. The information processing block 20 may include any required processing steps as known in the art to distinguish the particle of interest from the remaining suspension. The processing steps may vary depending upon the type of input received. The processing step, for example, may include simple recognition of a digital input value or may include complicated processing steps to detect whether a given input corresponds to the presence of a particle of interest.

After a particle is identified, the particle may be separated from the suspension by the actuation of separation block 30. The actuation may include, for example, steering an optical trap such as via a piezoelectric mirror, an acoustic optic deflector, a diffraction grating, a holographically-generated trap, a static line trap, a dynamic line trap, an optical gradient, a microlens array, a waveguiding structure or other known optical steering mechanism. The actuation may alternatively include generating an electric field or a magnetic field. The actuation may also include a mechanical or chemical actuator. A mechanical actuator, for example, may include a pump, valve, gate, applied pressure and the like. A chemical actuator, for example, may include a hydrogel or similarly behaving material that reacts to a property sensed in the suspension that may indicate the presence or absence of a particle of interest.

Each of the functions shown in blocks 10, 20 and 30 of FIG. 1, however, need not be performed by distinct hardware components. A sensor, for example, may receive an input and perform the information processing on that input to determine if a particle of interest has been detected. An actuator may even perform each of the functions by directly reacting to a property being monitored (e.g., a pH responsive hydrogel may swell in response to a sensed pH level).

Figure 2:
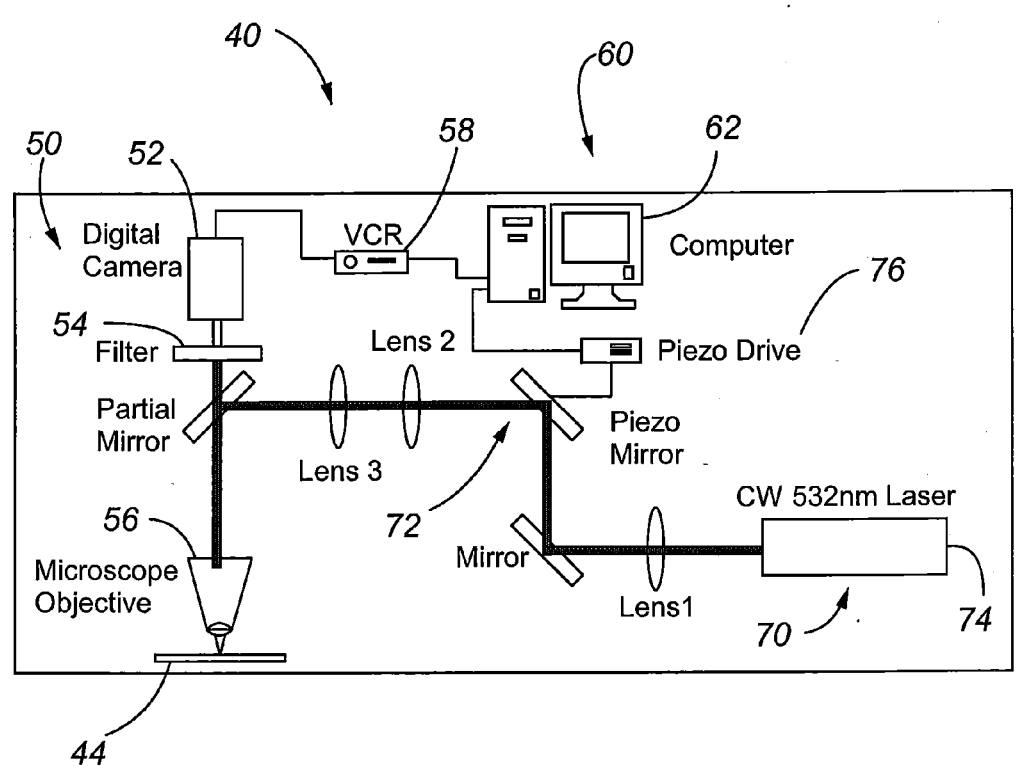
FIG. 2 depicts a block diagram of an exemplary system for separating a colloidal or cellular particle from a suspension in a microfluidic flow device.

FIG. 2 shows one exemplary system 40 for separating a particle of interest from a suspension in a microfluidic flow device 44 utilizing an actuated separation technique. The system includes an detector system 50, an information processing system 60 and an actuator system 70. The detector system 50 includes an imaging system, such as a camera 52, that may be used to image a field of view through a filter 54 and a microscope 56. The detector system 50, for example, may utilize a CCD camera to capture a stream of images of the microfluidic flow device through a microscope lens. In one particular embodiment, the camera 52 captures images at a rate of 30 images per second through a 100× objective. The images are recorded by a recording device, such as VCR 58, and/or passed directly to an information processor, such as a computer 62. Optionally, the identification of the particles may be aided by utilizing the laser 74 or another light source, such as a secondary laser, multiple other lasers, a broad spectrum lamp and the like, to irradiate the suspension to illuminate the particles of interest.

The information processor may include the computer 62, a controller or other processor known in the art. The information processor receives and processes the image data and distinguishes the particle of interest from the remaining suspension as described above. Once the particle is recognized, the information processor may trigger the actuator system 70 to separate the particle from the suspension.

The actuator system 70 may include a targeting device 72 to target a laser beam from a laser 74 on the microfluidic flow device 44. The targeting device, for example, may include a piezo drive 76 to control a piezo mirror 78 to direct the beam of a laser 74. The laser 74, when focused on the particle, traps the particle. The optical trap may then be used to translate the particle between streams in the channel of the microfluidic flow device 44.

Utilizing an optical trap as the means of actuation provides the capability for highly precise and immediately customizable individual separations. Other applied fields, however, may also be utilized to translate particles from the primary stream to the secondary stream. Both electric and magnetic fields may be employed with appropriate suspensions to isolate individual or multiple particles. All colloidal particles and living cells carry with them a surface charge, which, in the presence of an electrical field results in electrophoresis. The electrophoretic force, or the migration of surface ions with an electric field, is sufficient to translate cells or particles from one stream to another. Similarly, if a particle or cell possesses a magnetic moment, it may be selectively translated in a magnetic field. Each of these fields could be applied continuously to fractionate particles or cells based on electrical or magnetic properties, or could be pulsed or applied discriminatively for custom separations.

As described above, the suspension or the individual particles may be pretreated, as known in the art. The pretreatment, for example, may enhance the response of the particle to an optical trap or electric or magnetic field. The suspension may further be pretreated with items, such as antibodies that will bind specifically to a particular type of particle may be used to enable or enhance the movement of the particle via an optical trap or electric or magnetic field. A suspension of cells, for example, may be pretreated with antibody-decorated magnetic particles and, thus, be easily moved by means of a magnetic field.

Figure 2A:
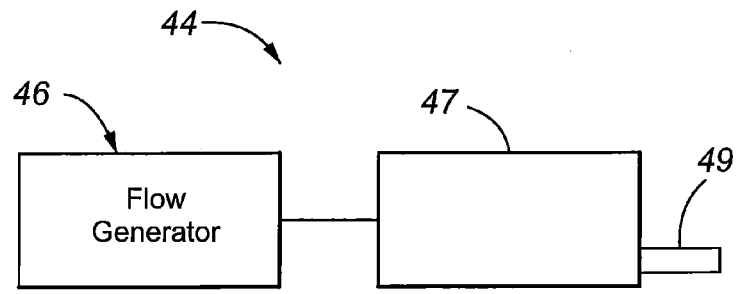
FIG. 2a depicts a block diagram of a microfluidic flow network that may be used in conjunction with the system depicted in FIGS. 2, 3 and 4.
Figure 3:
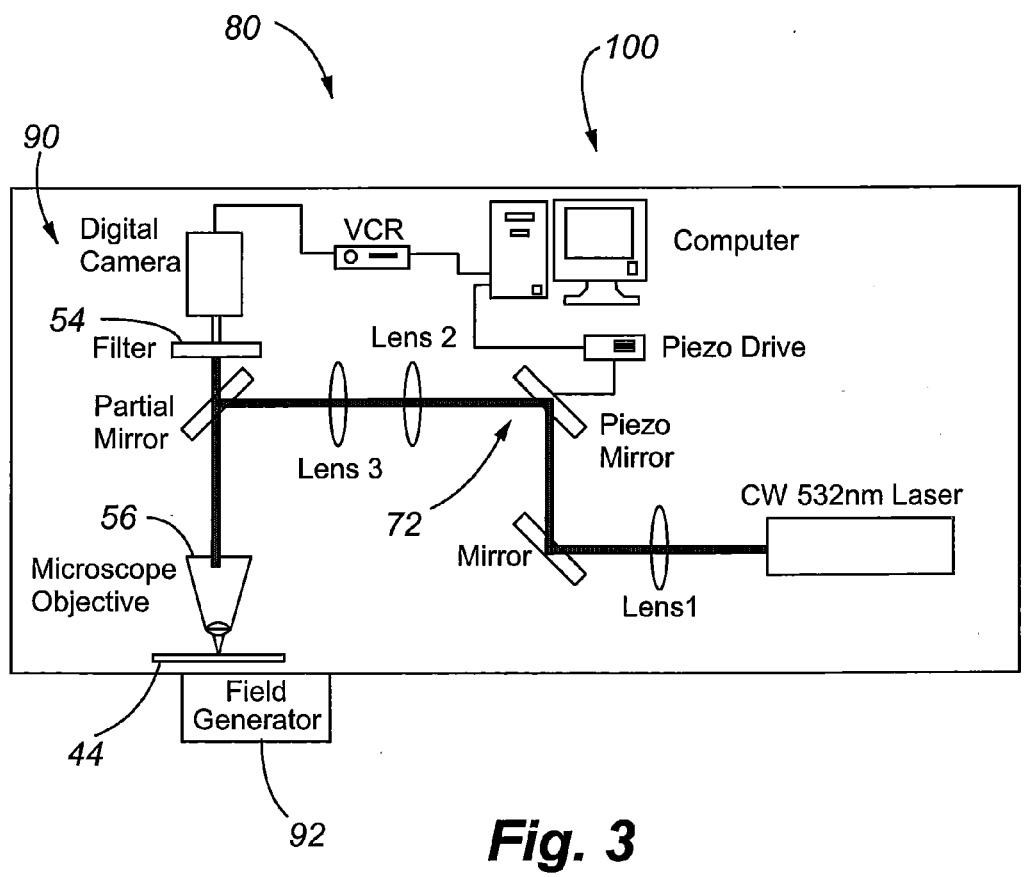
FIG. 3 depicts a block diagram of an alternative system for separating a colloidal or cellular particle from a suspension in a microfluidic flow device.
Figure 4:
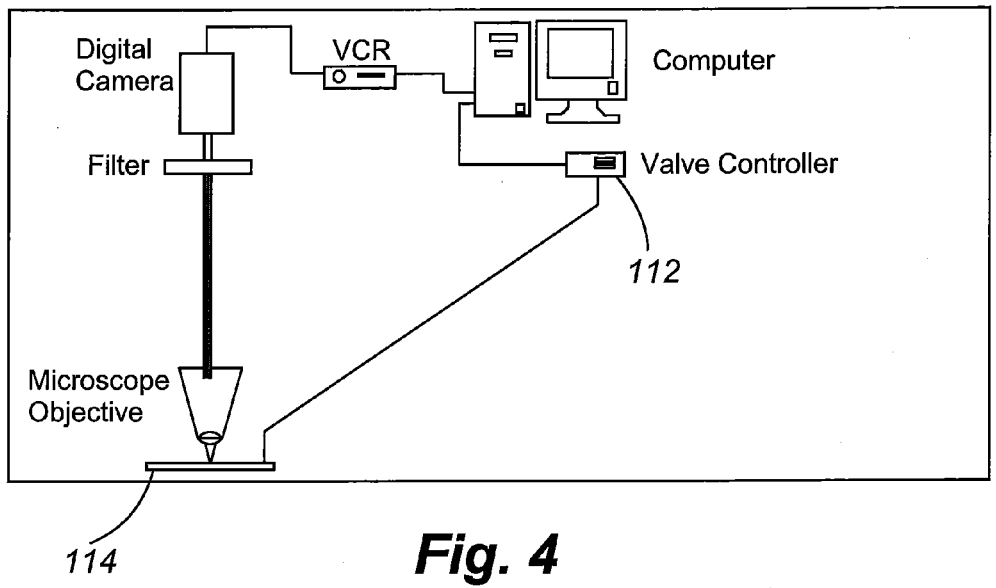
FIG. 4 depicts a block diagram of another alternative system for separating a colloidal or cellular particle from a suspension in a microfluidic flow device, wherein the system controls a valve actuator to separate the particle from the suspension.

FIG. 2a shows further detail of a microfluidic flow device 44 that may be used in connection with a system 40, 80 and 110 such as shown in FIGS. 2, 3 and 4, respectively. The microfluidic flow device 44 includes a flow generator 45, which provides a pressure differential to induce fluid flows through the microfluidic flow device 44. The pressure differential, for example, may be induced by any method known in the art such as, but not limited to, capillary forces; gravity feed; electro-osmosis systems; syringes; pumps such as syringe pumps (e.g., a kdScientific, model 200 syringe pump), peristaltic pumps and micropumps; valves such as three-way valves, two-way valves, ball valves and microvalves; suction; vacuums and the like. Further, although FIG. 2a shows the flow generator located upstream of a microfluidic flow chamber 47, the flow generator may also be placed midstream in the microfluidic flow chamber 47 or downstream of the microfluidic flow chamber 47. Further, the microfluidic flow chamber 47 preferably provides at least one output 49 with the collected particles separated from a suspension within the chamber. This output 49 may provide the collected particles as an end process or may provide the particles to a downstream network for further processing.

FIG. 3 shows an alternative system for separating a particle of interest from a suspension in a microfluidic flow device. The imaging system 90 and its operation is the same as shown in FIG. 2 except that the imaging system 90 further includes a field generator 92. The field generator 92 induces an electric or magnetic field in the microfluidic flow device 44. As the suspension flows through the device 44, the movement of the particles of interest, whether induced by electric or magnetic properties of the particles themselves or by properties associated with a pretreatment of the particles, is captured by the imaging system 90 and identified by the information processor 100.

FIG. 4 shows another system 110 for separating a particle of interest from a suspension in a microfluidic flow device 114. In this system, the actuator system includes a valve controller 112 that controls the operation of a valve within the microfluidic flow device 114. The valve, for example, may be opened to divert the flow of the suspension within the microfluidic flow device for a predetermined time after the recognition of the particle of interest. In this manner, the system separates the particle in a small portion of the suspension by diverting the suspension carrying the particle into an alternative outlet port. An example of such a valve is described below with respect to FIGS. 9a–9c.

A particular microfluidic flow channel can be modeled to determine the flow path of a fluid flowing in a laminar manner through the channel. This is well known in the art and involves solving the Langevin equations, the Navier-Stokes equations or other equations of motion, which can be done manually or electronically. Commercial software tools are also available for modeling the laminar flow path of a fluid through any microfluidic flow channel. For example, CFDASE, a finite element modeling for computational fluid dynamics module available from Open Channel Foundation Publishing Software from Academic & Research Institutions of Chicago, Ill., and FIDAP, a flow-modeling tool available from Fluent, Inc. of Lebanon, N.H., can be used to model the laminar flow of a fluid through a particular microfluidic channel.

Figure 5:
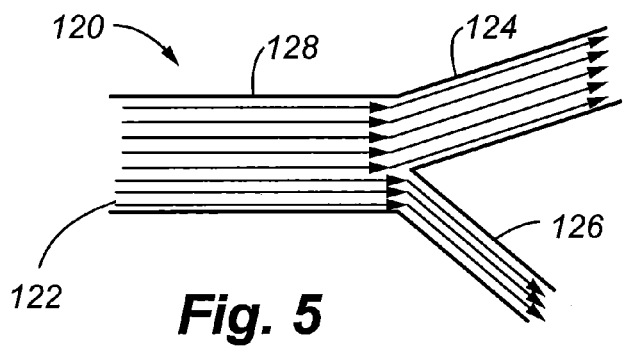
FIG. 5 depicts a fluid flow path in one example of a microfluidic flow chamber.
Figure 5A:
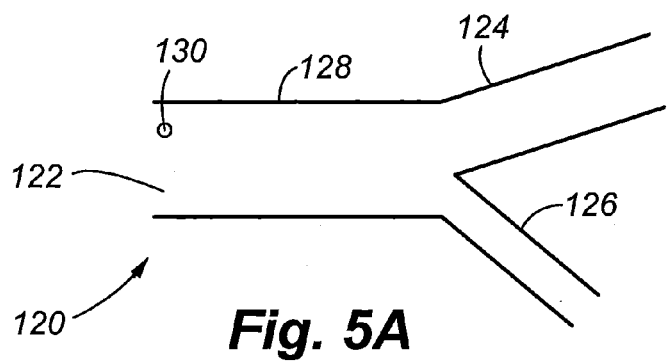
FIG. 5a depicts a particle entering the microfluidic flow chamber depicted in FIG. 5 via an inlet port.
Figure 5B:
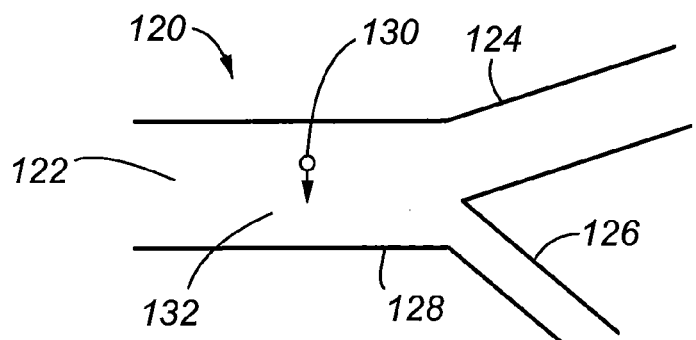
FIG. 5b depicts the particle depicted in FIG. 5a being moved within a central channel of the microfluidic flow chamber depicted in FIG. 5.
Figure 5C:
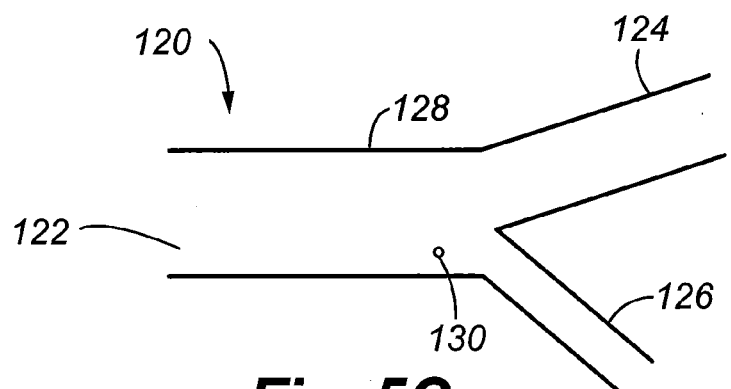
FIG. 5c depicts the particle depicted in FIG. 5a exiting the central channel of the microfluidic flow chamber depicted in FIG. 5 via an outlet port.

FIG. 5 shows an embodiment of a microfluidic flow chamber 120 in which a particle of interest may be separated from a suspension. The microfluidic flow chamber includes a single inlet port 122, two outlet ports 124 and 126 and a central channel 128. FIG. 5 further shows arrows depicting a modeled laminar flow of a particular fluid through the microfluidic flow chamber 120. FIG. 5a–5c show a process for separating a particle 130 from a suspension flow in the microfluidic flow chamber 120 of FIG. 5. FIG. 5a shows the particle entering the microfluidic flow chamber 120 via the inlet port 122 at which point it is identified as described above. The information processor initiates an actuator to direct the particle 130 into a desired portion of the flow stream 132 of the suspension in FIG. 5b. Thus, the particle 130 is directed to a portion of the flow in which it will exit the central chamber 128 through the second outlet port 126, as shown in FIG. 5c.

Figure 6:
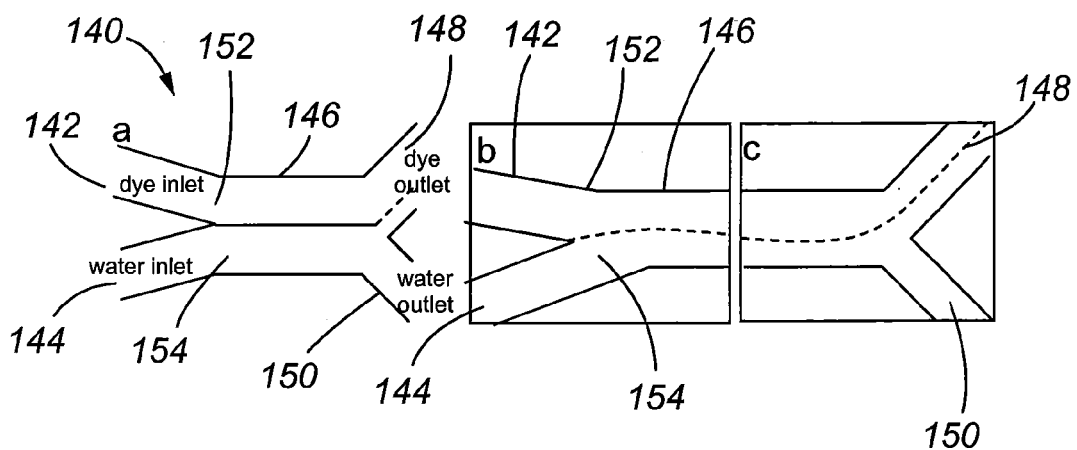
FIG. 6 depicts side-by-side laminar fluid flows in the central channel of the microfluidic flow chamber depicted in FIG. 5.

FIGS. 6 and 6a–6c show an alternative embodiment of a microfluidic flow chamber 140, which includes two inlet ports 142 and 144, a central channel 146 and two outlet ports 148 and 150. As FIG. 6 shows, a first fluid 152, indicated by dye, enters the central channel 146 via the first inlet port 142 and a second fluid 154 enters the central channel 146 via the second inlet port 144. As described above, when the first fluid 152 and the second fluid 154 flow through the microfluidic flow chamber in a laminar manner, the fluids maintain separate streams and undergo minimal convective mixing. Rather, the mixing present is primarily due to molecular-scale diffusion, which for colloidal-sized particles is referred to as Brownian movement, as shown near the outlet port of the central channel. The system can be designed to minimize the diffusion that occurs within the central channel 146 by controlling the central channel 146 dimensions and the velocity of the fluid flowing through the channel 146. In general, the diffusion distance x, can be expressed as $x \approx \sqrt{D \cdot t}$, wherein D is the diffusivity and t is the time. To a first order, the diffusivity is inversely proportional to the size of the particle. Therefore, to a first order, the channel residence time required to achieve complete mixing, $t \approx x^2 D^{-1}$, scales linearly with the particle diameter. Thus, by designing the microfluidic flow chamber dimensions for a particular flow rate of a fluid, a laminar two-phase flow may be used as an effective barrier against particle cross-transport. In the example shown in FIG. 6, each of the inlet streams has a width of about 30 μm and the central channel has a length from the inlet ports to the outlet ports of about 3000 μm, the reduction of which will correspondingly reduce the diffusion within the channel 146 for a constant flow rate. Both of the fluids streams 152 and 154 shown are water. The first stream 152 includes a molecular dye (Methylene Blue), which has a diffusion coefficient on the order of about $1 \times 10^{-5}$ cm$^2$/sec in water.

Figure 6A:
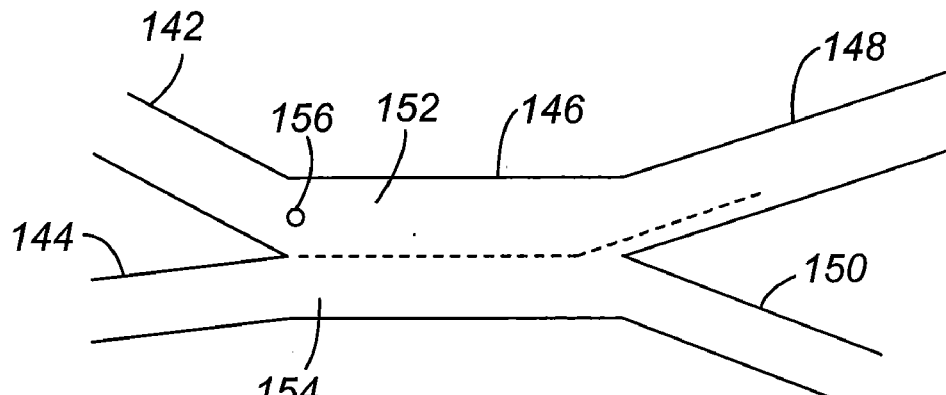
FIG. 6a depicts a particle entering the central channel via an inlet port of the microfluidic flow chamber in the first fluid flow depicted in FIG. 6.

Further, as shown by the dashed line in FIG. 6a, a portion of the second fluid stream 154 can exit the central channel 146 via the first outlet port 148 while the remainder of the second fluid 154 exits via the second outlet port 150. If the first fluid 152 is a suspension including suspended particles and the second fluid 154 is a clean solvent, for example, the portion of the solvent that exits the first outlet port 148 along with the suspension 152 acts as an additional barrier to cross-contamination of the streams through diffusion. Thus, particles that diffuse into this portion of the solvent stream may still exit the central chamber 146 via the first outlet port 148, as shown in FIG. 6.

The steady state flow-based particle barrier can be penetrated, however, by providing an actuator to move a particle 156 across the barrier. A selective activation of an electric, magnetic or optical field, or any combination of these fields, for example, may be used to move the particle 156 from one stream to another stream. Alternatively, a mechanical actuator, such as a valve, pump, gate or applied pressure may be employed to move the particle from one stream to another stream. Although described here for parallel flows, the flows traveling in arbitrary orientations, including opposite directions, are possible.

Figure 6B:
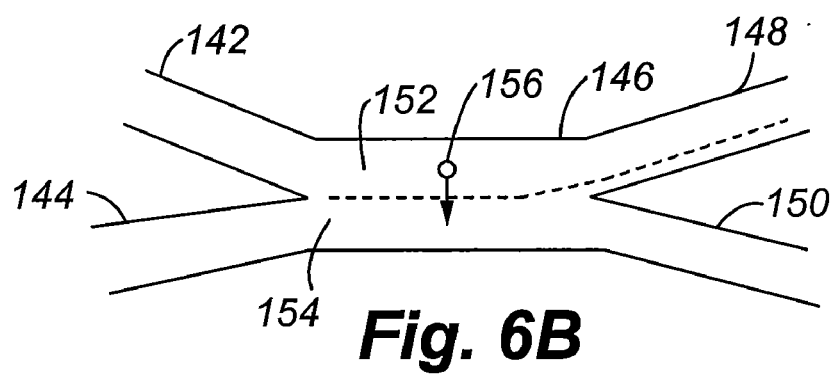
FIG. 6b depicts the particle depicted in FIG. 6a being moved within the central channel of the microfluidic flow chamber from the first flow to the second flow.
Figure 6C:
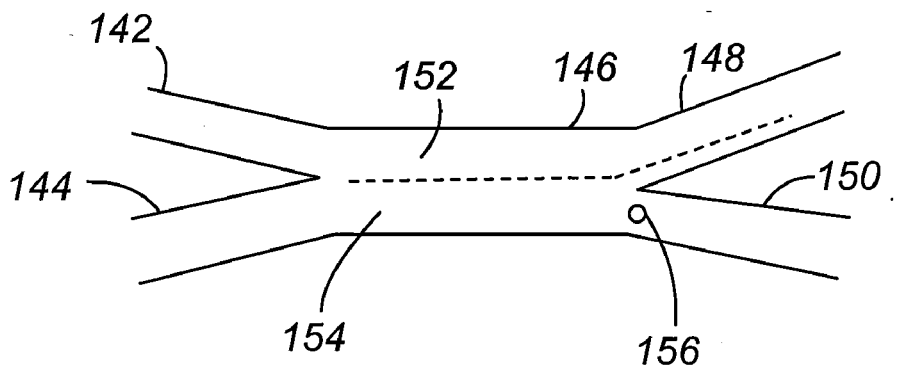
FIG. 6c depicts the particle depicted in FIG. 6a exiting the central channel of the microfluidic flow chamber in the second flow via an outlet port.

FIGS. 6a–6c show a particle 156 being separated from the first inlet stream 152 into the second inlet stream 154 in the embodiment shown in FIG. 6. In FIG. 6a, a suspension enters the central channel 146 from the first inlet port 142, and a second fluid 154, such as a solvent, enters the central channel 146 from the second inlet channel 144. The suspension 152 and the second fluid 154 flow in a laminar manner through the central channel 146. The suspension stream 152 and a portion of the second fluid stream 154 exit the central channel 146 via the first outlet port 148. The remaining portion of the second fluid stream 154 functions as a collection stream and exits the central channel 146 via the second outlet port 150. A particle 156 suspended in the suspension stream 152 is shown entering the central channel 146 from the first inlet port 142, where it is identified as described above. In FIG. 6b, the particle 156 is shown being separated from the suspension stream 152 into the second fluid stream 154. The particle 156 may be separated from the suspension 152 via an electrical, magnetic, mechanical or chemical actuator such as described above. In FIG. 6c, the particle 156 is shown exiting the central channel 146 via the second outlet port 150 in the second fluid stream 154 for collection.

Figure 7:
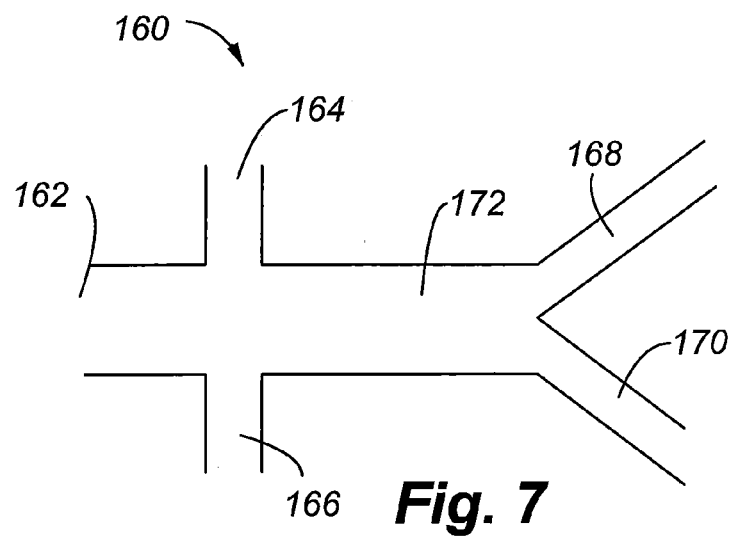
FIG. 7 depicts an alternative example of a microfluidic flow chamber.
Figure 7A:
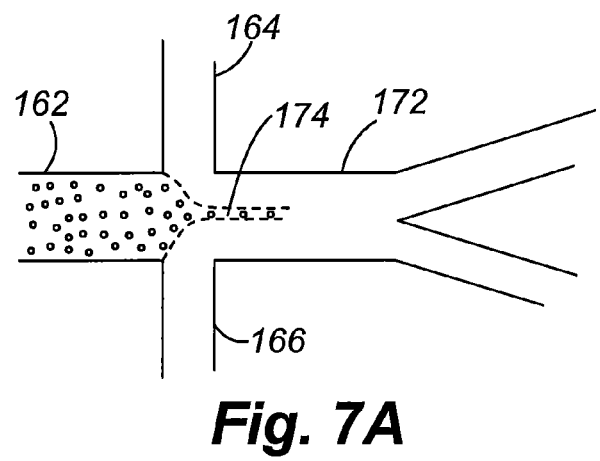
FIG. 7a depicts side flows pinching a central flow of a suspension at the entrance to a central channel of the microfluidic flow chamber depicted in FIG. 7 to orient the flow of suspension in the center portion of the channel.
Figure 7B:
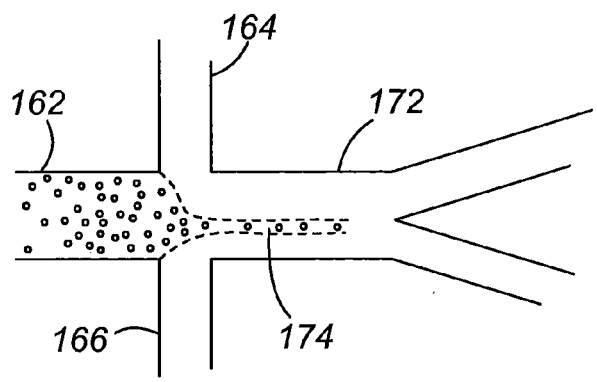
FIG. 7b depicts side flows pinching a central flow of a suspension at the entrance to a central channel of the microfluidic flow chamber depicted in FIG. 7 to orient the flow of suspension in the bottom portion of the channel.
Figure 7C:
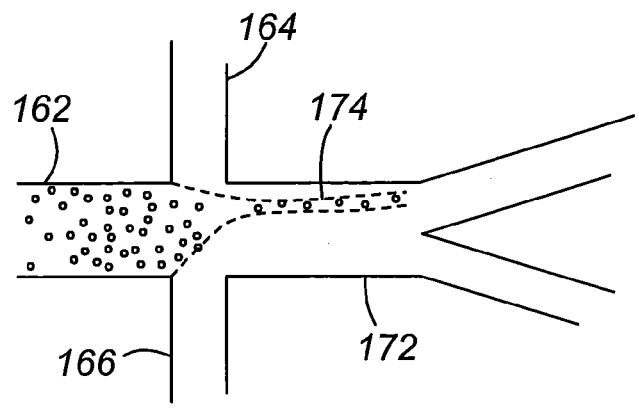
FIG. 7c depicts side flows pinching a central flow of a suspension at the entrance to a central channel of the microfluidic flow chamber depicted in FIG. 7 to orient the flow of suspension in the top portion of the channel.

FIG. 7 shows another embodiment of a microfluidic flow chamber 160 in which a particle of interest may be separated from a suspension. The microfluidic flow chamber 160 includes three inlet ports 162, 164 and 166, two outlet ports 168 and 170 and a central channel 172. In this example, a suspension including suspended particles enters from the first inlet port 162. Other fluid streams, such as a pair of solvent or buffer fluid streams enter the central channel 172 from either side of the first inlet port 162. As shown in FIGS. 7a–7c, the relative flow rates of each inlet port may be modulated to vary the resulting incoming stream 174 into the central channel 172. In FIG. 7a, for example, the relative flow rates of the streams in the second inlet port 164 and the third inlet port 166 are relatively equal and pinch the flow from the first inlet port 162 at a neck and form a narrow stream of the first fluid approximately down the center of the central channel 172. By varying the flow rates of the second and third inlet streams 164 and 166, the width of the first fluid stream 174, i.e., the suspension, can be narrowed down to the width of a single particle. Thus, the inlet sample suspension 174 may be "prefocused" into a narrow, or even single file, particle stream surrounded on either side by a potential collection stream. This allows for a decrease in the lateral distance, i.e., distance perpendicular to the flow direction, a particle must be moved away from the suspension stream to be captured in the collection stream and, thus, an increase in sorting efficiency.

FIG. 7b shows the embodiment of FIG. 7, wherein the flow rate of the third inlet port 166 is less than the flow rate of the second inlet port 164 and prefocuses the inlet particle stream in the lower half of the central chamber 172. Conversely, FIG. 7b shows the embodiment of FIG. 7, wherein the flow rate of the third inlet port 166 is greater than the flow rate of the second inlet port 164 and prefocuses the inlet particle stream in the upper half of the central chamber 172. The relative flow rates of the three inlets can thus be modulated to control the particle stream within the central channel.

Figure 8:
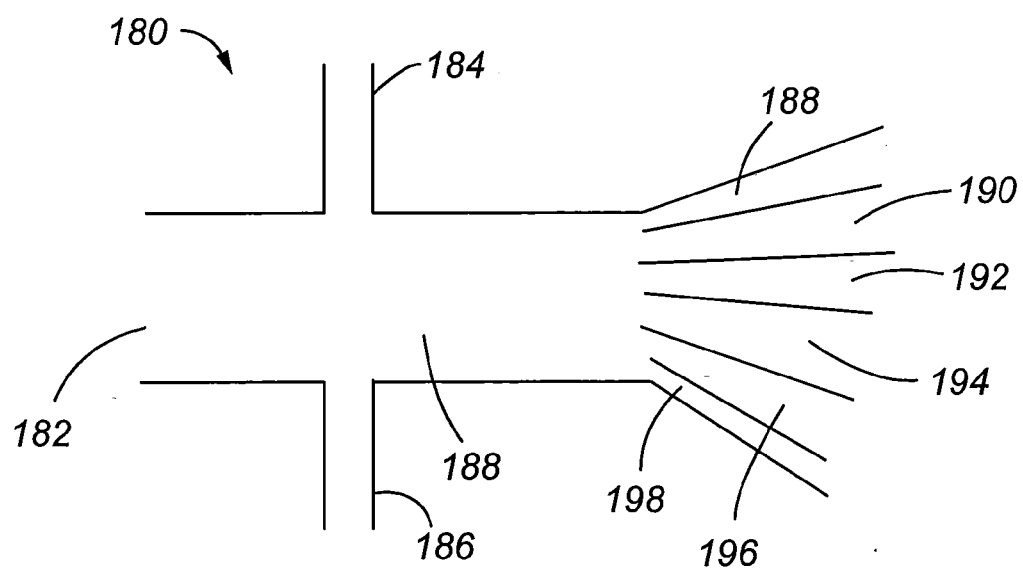
FIG. 8 depicts another example of a microfluidic flow chamber including a plurality of outlet ports for sorting colloidal and/or cellular particles in a suspension.

FIG. 8 shows yet another embodiment of a microfluidic flow chamber 180 in which a particle of interest may be separated from a suspension. As in FIG. 7, the microfluidic flow chamber 180 includes three inlet ports 182, 184 and 186 and a central channel 188. The chamber 180 of FIG. 8, however, includes six outlet ports 188, 190, 192, 194, 196 and 198. The number of outlet ports shown in FIG. 8 is merely exemplary and may include any number of outlet ports greater than or equal to two. In this example, the plurality of outlet ports may be used to sort a plurality of particles into various outlet ports. Different types of particles, for example, may be sorted into different outlet ports. Alternatively, the plurality of outlet ports may be used to individually sort the same type of particles into different outlet ports. In yet another embodiment, the side flows may be modulated as described above to dispense particles, chemicals and/or fluids (e.g., reagents) into multiple outlet ports for use in various downstream applications or networks.

Alternatively, the incoming streams may be prefocused prior to entry into the microfluidic flow chamber, or the side inlet ports may be arranged to enter the central channel downstream of the first inlet port.

Figure 9:
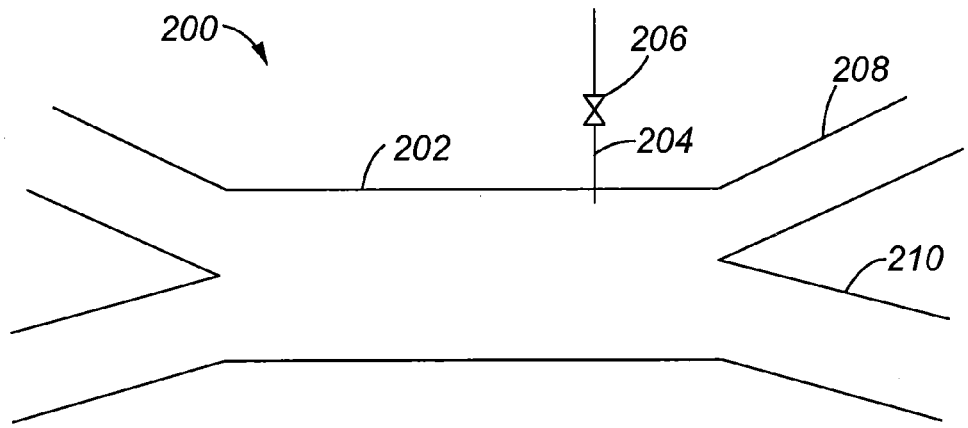
FIG. 9 depicts a microfluidic flow chamber including a mechanical actuator for separating a colloidal and/or cellular particle in a suspension, wherein the mechanical actuator comprises a valve.

FIG. 9 shows an embodiment of a microfluidic flow chamber 200 in which a particle of interest may be separated from a suspension via a mechanical actuator. As shown in FIG. 9, the central channel 202 includes a side channel 204 through which incoming fluid flow is controlled by a valve 206. After a particle is detected, the valve may be opened to vary the fluid flow within the central channel 202 and divert the suspension along with the particle away from the first outlet port 208 into the second outlet port 210. Alternatively, the valve 206 may be closed or the flow through the valve may be merely adjusted to divert the particle into the desired outlet port. Similarly, the valve 206 may be positioned on the opposite side of the central chamber 202 and may obtain a similar result by providing or modulating the flow in the opposite direction.

Figure 9A:
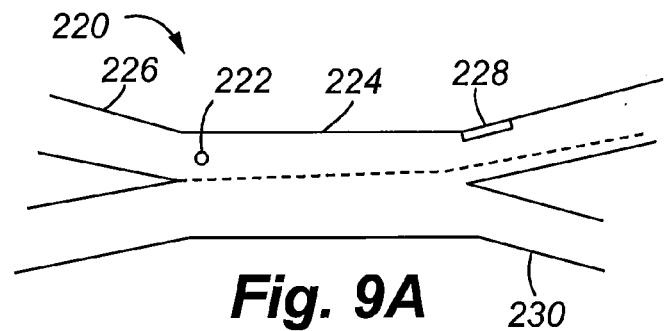
FIG. 9a depicts an alternative example of a microfluidic flow chamber including a mechanical actuator for separating a colloidal and/or cellular particle in a suspension, wherein the mechanical actuator comprises a valve.
Figure 9B:
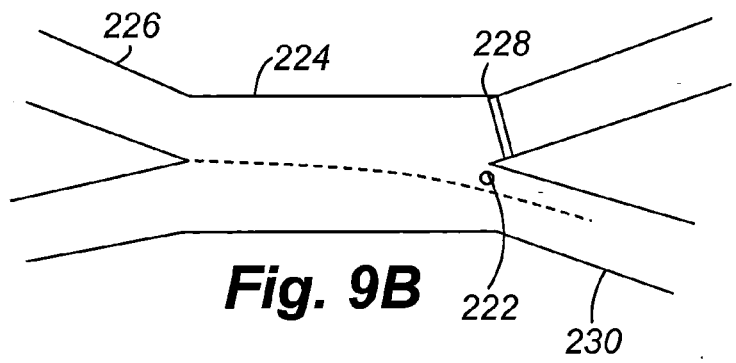
FIG. 9b depicts the particle being separated from the suspension via the valve of the microfluidic chamber depicted in FIG. 9a being closed to divert the particle into an alternative outlet port.
Figure 9C:
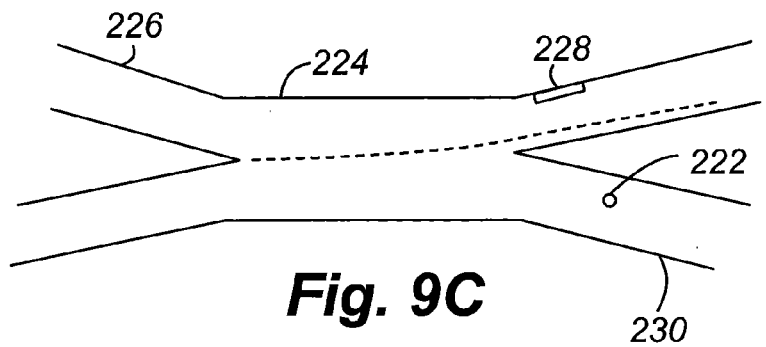
FIG. 9c depicts the particle exiting the alternative outlet port of the microfluidic chamber depicted in FIG. 9a and the valve retracting to its open position.

FIGS. 9a–9c show yet another embodiment of a microfluidic flow chamber 220 in which a particle of interest may be separated from a suspension via a mechanical actuator. As shown in FIG. 9a, the particle 222 enters the central channel 224 in the suspension via the first inlet port 226. In FIG. 9b, the valve 228 activates after the particle is identified as described above and redirects the particle 222 into the second outlet port 230. Then, in FIG. 9c, after the particle 222 has exited the central channel 224, the valve 228 retracts and the fluid stream flows return to their steady state condition.

Figure 9D:
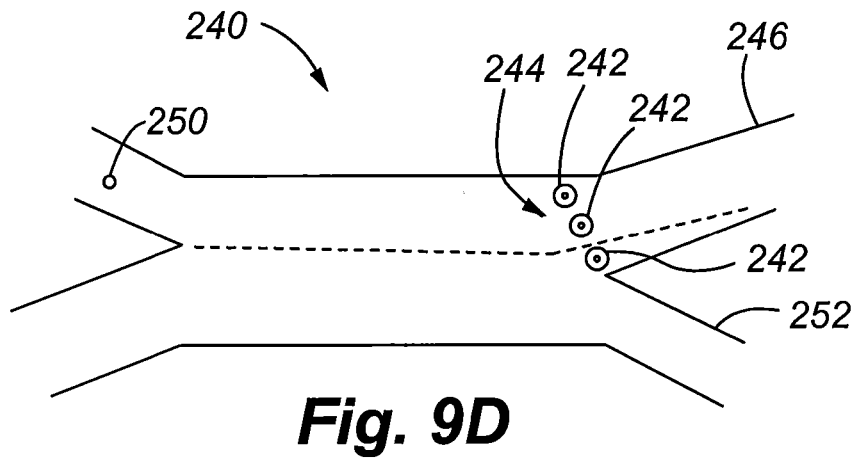
FIG. 9d depicts another alternative example of a microfluidic flow chamber including a chemical actuator for separating a colloidal and/or cellular particle in a suspension, wherein the chemical actuator comprises a chemically actuated valve.
Figure 9E:
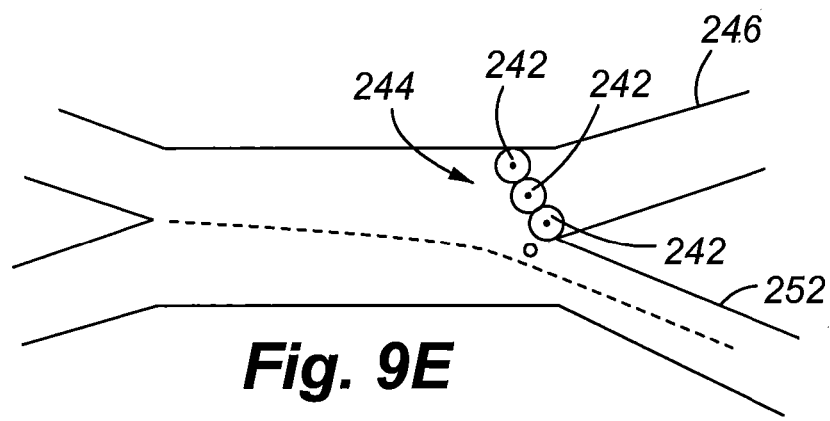
FIG. 9e depicts the particle being separated from the suspension via the valve of the microfluidic chamber depicted in FIG. 9d being swollen closed to divert the particle into an alternative outlet port.
Figure 9F:
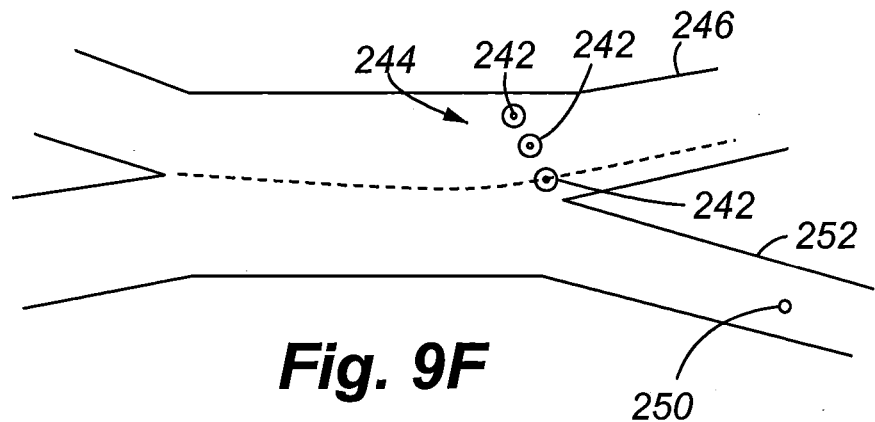
FIG. 9f depicts the particle exiting the alternative outlet port of the microfluidic chamber depicted in FIG. 9d and the valve shrinking to its open position.

FIGS. 9d–9f show an exemplary microfluidic flow chamber 240 in which a particle of interest may be separated from a suspension via a chemical actuator. As shown in FIGS. 9d–9f, the microfluidic flow chamber 240 includes a chemical actuator material 242, such as a hydrogel, that swells or shrinks in reaction to an attribute associated with a particular particle of interest (e.g., pH). Hydrogels, such as these are known in the art. Beebe, David J. et al, "*Functional Hydrogel Structures for Autonomous Flow Control Inside Microfluidic Channels, Nature,* vol. 404, pp. 588–90, (Apr. 6, 2000), for example, discloses hydrogel actuators that may be used in the present embodiment.

FIGS. 9d–9f show a chemically actuated valve 244 including the chemical actuator material 242. In FIG. 9d, for example, the chemical actuator is in its normal condition in which the valve 244 is open and the suspension flows through the first outlet port 246. FIG. 9e shows the chemical actuator in its active state in which the chemical actuator material 242 is swollen in response to a detected attribute, effectively shutting off the first outlet port 246 and the suspension flows through the second outlet port 252 and allowing the particle 250 of interest to be collected. Although FIG. 9e shows the chemically actuated valve 244 completely closing off the first outlet port, the swelling of the chemically actuated material 242 may also merely create a barrier to particular-sized particles while allowing the remainder of the suspension to pass into the first outlet port 246. Where the individual valve members are angled toward the second outlet port 252, the blocked particles 250 may be conveyed to the second outlet port 252 for collection. FIG. 9f further shows the chemically actuated valve 244 returned to its open condition after the detected particle 250 has passed into the second outlet port 252.

Alternatively microfluidic flow devices may employ laminar flows and specific microgeometries for non-actuated separation of colloidal and/or cellular particles in fluid suspensions. The geometry of these devices has been designed to act similarly to a filter without the use of membranes or sieves which are highly susceptible to clogging and fouling. Such devices will also be capable of replacing the centrifugation step common to many biological processes upon a chip surface. With a microscale alternative to centrifugation available, a host of multi-step biological processes such as bead-based assays and cell counting using dying techniques will be able to be performed within microfluidic devices.

Figure 10:
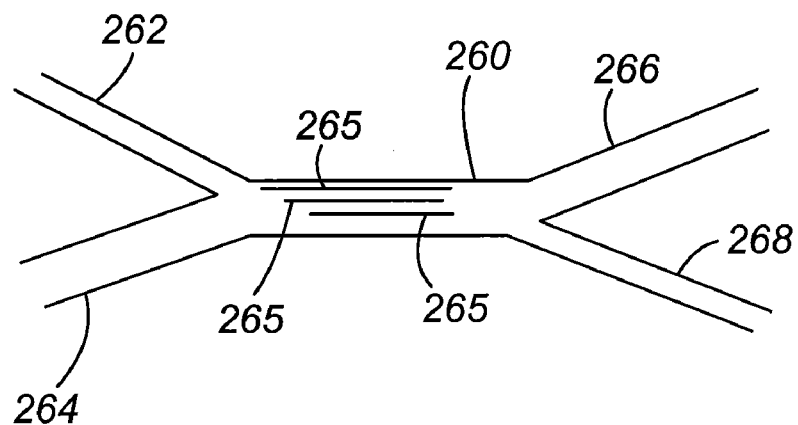
FIG. 10 depicts a series of suspensions being introduced into a microfluidic flow chamber in series separated by buffers.
Figure 11:
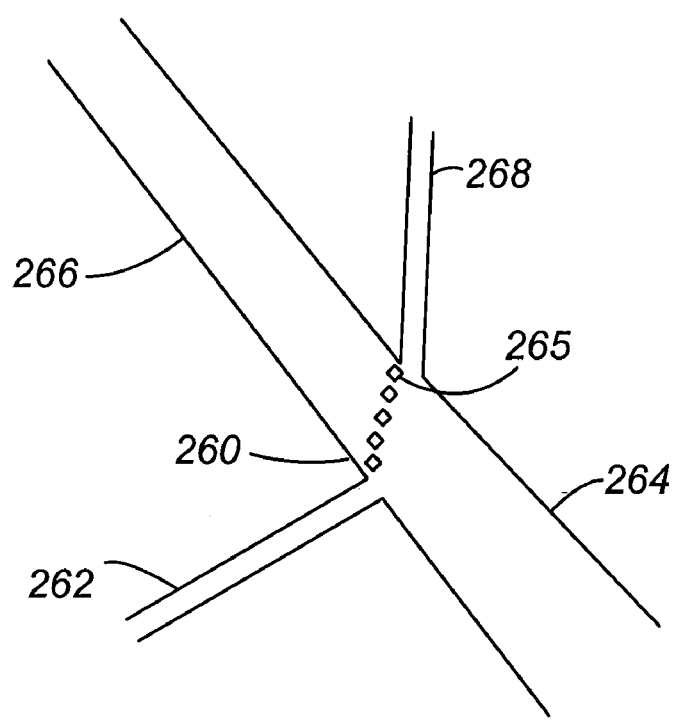
FIG. 11 depicts an alternative non-actuated microfluidic flow device for separating colloidal and/or cellular particles from a suspension.
Figure 12:
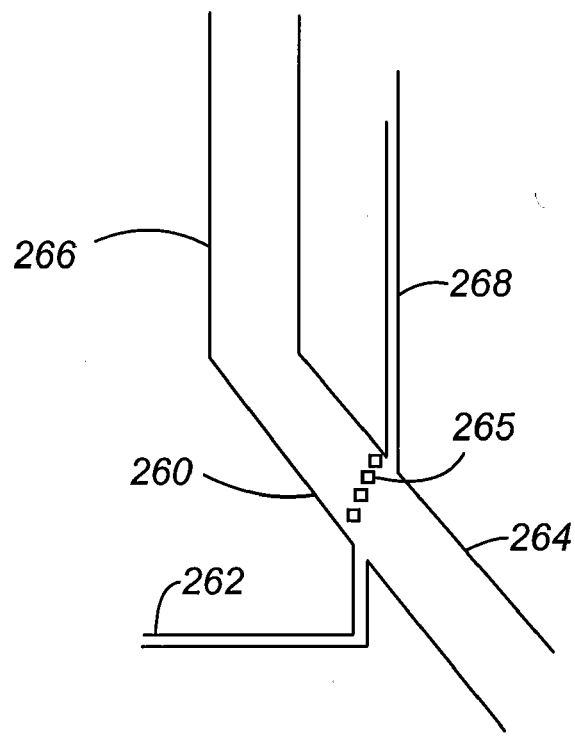
FIG. 12 depicts another alternative non-actuated microfluidic flow device for separating colloidal and/or cellular particles from a suspension.

As demonstrated in FIGS. 10 12, specific channel geometries may be created to take advantage of the laminar nature of fluids flowing in microchannels. In each of these designs, the particle suspension enters the central channel 260 through a first inlet port 262. A second fluid stream, such as a solvent stream, enters the channel 260 through a second inlet port 264, which meets the first inlet port 262 at any angle. Because of the laminar nature of microfluidic flows, these streams will generally not mix convectively. The central channel 260 further includes microscale obstacles 265. Molecular debris small enough to fit through the openings formed by the microscale obstacles 265 will be carried down the first outlet port 266. Due to the presence of microscale obstacles, however, any particles larger than the separation of the obstacles will be shuffled toward the second outlet port 268 and exit the central channel 260 with a portion of the second fluid stream. The designs shown here do not depend upon relative channel size, instead the presence of the microscale obstacles at or near the confluence of the two (or more) inlet streams alter the direction of flow for any particulate matter in the suspension inlet stream(s).

Figure 13:
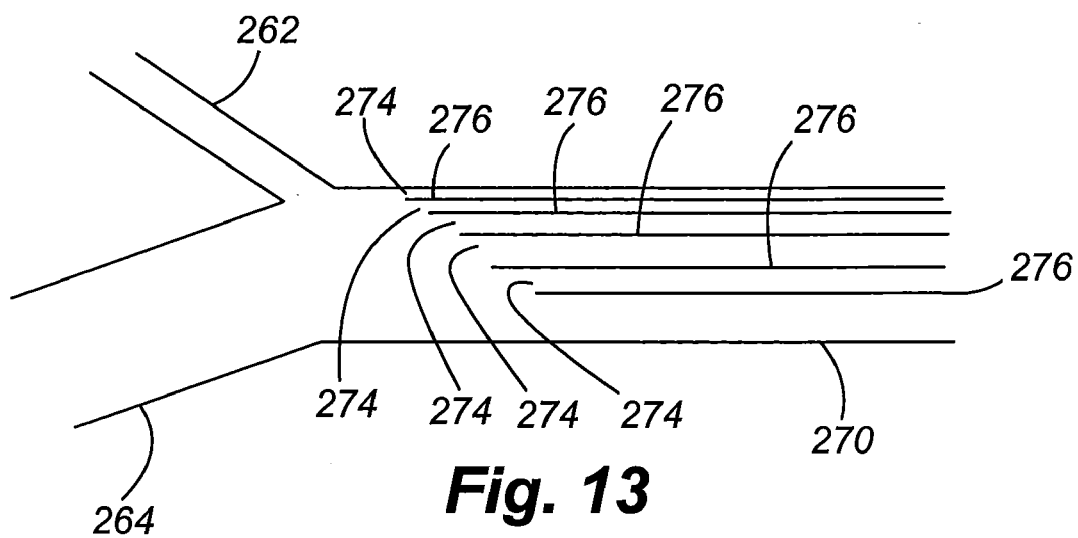
FIG. 13 depicts an exemplary non-actuated microfluidic flow device for sorting colloidal and/or cellular particles from a suspension by size.

FIG. 13 further shows a configuration for sorting particles in the suspension by size and produces a size fractionation effect by designing the size of the gaps 274 between the guides 276 to increase away from the first inlet port 262, by which the suspension is introduced into the central channel 270. By gradually increasing the widths of the gaps 274 moving away from the first inlet port 262, particles of increasing size flow into the guides 276 and may be collected individually.

Figure 14:
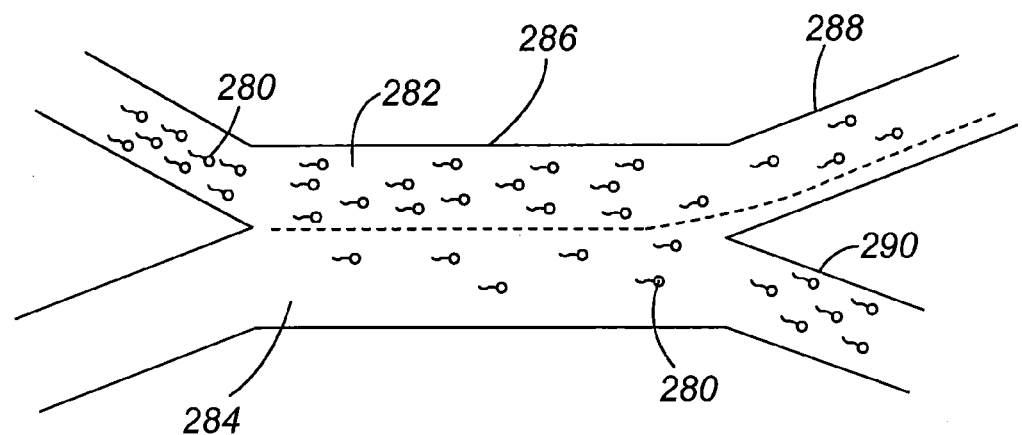
FIG. 14 depicts an alternative non-actuated microfluidic flow device for separating motile cellular particles from a suspension.

FIG. 14 shows yet another embodiment of a non-actuated separation of motile particles within a suspension between laminar flows. In this embodiment, motile particles 280 entering in the suspension flow 282 move within the suspension flow and can pass from the suspension flow 282 into the second fluid stream 284 without the need of an actuator to separate the particles 280 from the suspension flow 282. In this manner, the motile particles 280 may enter the second fluid stream 284 and exit the central channel 286 through the second outlet port 290 instead of the first inlet port 288. For example, in a suspension 282 containing sperm, the active sperm may move on their own into the second fluid stream 284 for collection, while inactive sperm are carried out of the central channel 286 with the suspension 282 via the first outlet port 288.

Non-actuated separation of colloidal and/or cellular particles from a suspension in a microfluidic flow device presents a very simple approach to microfluidic separations or enrichments of colloidal and/or cellular particles because it relies upon the condition native to fluids flowing on the microscale, regardless of flow rate or channel morphology: laminar flows. Furthermore, the selection of materials for the construction of these devices is irrelevant, thus they may be incorporated into microfluidic devices constructed on any substrate.

Figure 15:
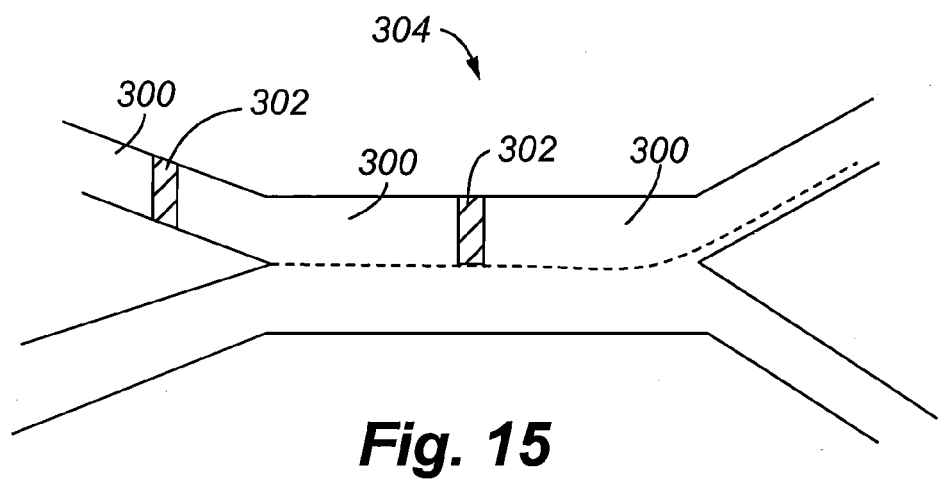
FIG. 15 depicts an exemplary non-actuated microfluidic flow device for separating colloidal and/or cellular particles from a suspension.

FIG. 15 shows another example of a microfluidic flow chamber in which a series of discrete sample suspensions 300 are combined into a single laminar flow. In this example, a plurality of discrete samples 300 form the single sample flow. The sample flow further preferably includes buffers 302 between each discrete sample 300 to prevent cross-contamination between samples 300. In this manner, a single microfluidic flow chamber 304 can separate particles from a series of samples to increase throughput. The series of discrete sample suspensions may, for example, be created using a microfluidic dispenser as shown and described above with reference to FIG. 8 in which individual samples are directed into a plurality of outlet ports and combined downstream into a series of discrete sample streams.

Figure 16:
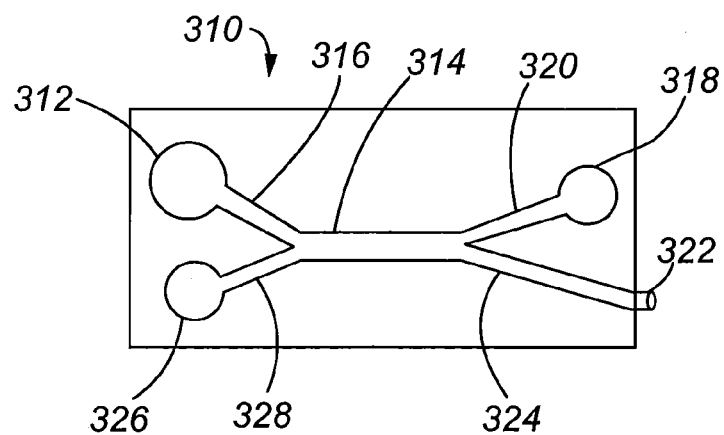
FIG. 16 depicts a cartridge including a microfluidic flow chamber.

FIG. 16 shows a cartridge 310 that may be plugged into, or otherwise connected to, a system for separating one or more colloidal or cellular particles from a suspension. The cartridge 310 may be reusable or disposable. The cartridge may include a sample reservoir 312, or other inlet mechanism, for receiving a fluid suspension. The sample reservoir 312 is connected to a central channel 314 via a first inlet port 316. The cartridge further includes a waste receptacle 318, or other outlet mechanism, connected to the central channel 314 via a first outlet port 320 for receiving the suspension after it has passed through the central channel 314 for the removal of one or more particles of interest. A collection receptacle 322 is also connected to the central channel 314 via a second outlet port 324 for receiving the particles collected from the suspension. The collection receptacle 322 may include a reservoir or other means for holding the collected particles or may include a channel or other means for providing the collected particles to downstream networks for further processing.

The cartridge 310 may also include a second inlet reservoir 326 for receiving a second fluid, may receive the second fluid from an external source in the system, or may not utilize a second fluid at all, such as described with reference to FIG. 5. If used, the second fluid may include a fluid such as a buffer or a solvent (e.g., water, a saline suspension and the like) or a reagent (e.g., antibody tagged particles, fluorescent tags, lysing agents, anticoagulants and the like), or any combination thereof. Indeed, the fluid requirements may be system-specific and may be matched to the intended application and mode of use. The second inlet reservoir 326 or receptacle for receiving a second fluid, if used, may be connected to the central channel 314 via a second inlet port 328.

The reservoirs or receptacles may include any interface for transferring a fluid known in the art. For example, the reservoir may be adapted to receive fluids from a syringe, either with or without a needle, from a tube, from a pump, directly from a human or animal, such as through a finger stick, or from any specially designed or standard fluid transfer coupling.

The microfluidic flow chambers described herein may be manufactured by a variety of common microelectronics processing techniques. A pattern of a shadow mask may be transferred to a positive or negative photoresist film spun upon a silicon wafer, a glass slide, or some other substrate, for example. This pattern may be sealed and used directly as the microfluidic network, replicated in another material, or further processed. The substrate may be further processed through subsequent wet etching, dry etching, molecular epitaxy, physical deposition of materials, chemical deposition of materials, and the like, or any combination of these or similar techniques. The final network may be used directly or reproduced through the use of a replication technique designed to produce a replica upon the master, such as by the pouring and curing, imprinting in or deposition of elastomers, polymers and the like. A pump or other means for introducing and controlling fluid flow within the fluidic network as well as a means for connecting the pump or pressure differential means may also be provided. The network can further be sealed, such as with a cover slip, glass slide, silicon wafer, polymer films or a similar substrate.

In one specific, nonlimiting example, a pattern on a shadow mask was exposed to ultraviolet light and transferred to a negative photoresist film spun upon a silicon wafer to a depth of approximately 5 μm. A two-part mixture of poly(dimethyl siloxane) (PDMS), which is commercially available from Dow Corning under the trade name of Sylgard 184, was poured and cured upon the silicon master to produce a flexible, biocompatible optically transparent replica. In addition to the PDMS channel network a flow apparatus comprising a syringe pump such as a kdScientific, model 200 syringe pump and a polymethyl methalacrylate (PMMA) flow introduction base. The PDMS channel network was placed upon the PMMA base, and holes were punched through the PDMS to provide access for the microchannels to the ports in the base. The network was further sealed with a cover slip. Because the PDMS forms a tight seal with both PMMA and glass, no additional bonding or clamping was required. The syringe pump was further fitted with 3 cm$^3$ plastic syringes (such as available from Becton-Dickson) joined to the base.

One embodiment of an optical trap and digital microscopy that may be used with the microfluidic flow devices described herein may incorporate a piezoelectric mirror (such as available from Physik Instrumente, model S-315) to simultaneously trap several particles by rapidly scanning a single laser beam (such as available from Spectra Physics, 532 nm, typically operated at 200 mW) among a number of positions to create a time-averaged extended trapping pattern. A Neofluar, 100X, oil immersion high numerical aperture objective (N.A.=1.30) can be used to focus the beam and create the optical trap. CCD images can be captured by a data acquisition board and processed by LabView (National Instruments) routines that may be customized to distinguish various visual particle or cell features for specific applications. Optical traps and digital microscopy are described in further detail, for example, in Mio, C.; Gong, T.; Terry, A.; Marr, D. W. M., Design of a Scanning Laser Optical Trap for Multiparticle Manipulation, Rev. Sci. Instrum. 2000, 71, 2196–2200.

While the invention has been particularly shown and described with reference to particular embodiment(s) thereof, it will be understood by those skilled in the art that various other changes in the form and details may be made without departing from the spirit and scope of the invention. One skilled in the art of microfluidic flows, for example, would recognize that downstream or upstream analogues of mechanisms described herein may be substituted for the particular exemplary structures disclosed herein.

The invention claimed is:

1. A method of separating one or more larger cells from one or more smaller cells in a first fluid flow, comprising:
   receiving the first fluid flow comprising said one or more larger cells and said one or more smaller cells in a microfluidic channel;
   optionally receiving a second fluid flow in the channel adjacent to said first fluid flow, the first fluid flow and the second fluid flow both flowing under laminar conditions in the channel;
   separating said one or more larger cells from said first fluid flow using a plurality of obstacles, said obstacles differentially deflecting said one or more larger cells to a first outlet port by physically contacting said one or more larger cells, wherein each of said plurality of obstacles is staggered in position as compared to an upstream obstacle;
   directing at least a portion of said first fluid flow through a second outlet port; and
   directing said one or more larger cells through said first outlet port.

2. The method of claim 1, wherein the laminar conditions are characterized by a Reynolds number of less than about 1000.

3. The method of claim 1, further comprising providing a pressure differential for providing fluid flow in said microfluidic channel.

4. The method of claim 3, wherein the pressure differential is provided by one or more of a group comprising a pump, a capillary force generator, a gravity feed generator, an electro-osmosis system, a syringe, a valve, a suction generator, and a vacuum generator.

5. The method of claim 1, wherein separating comprises passing the first fluid flow through a plurality of obstacles adapted for differentially directing said one or more larger cells into said first outlet port and said one or more smaller cells into said second outlet port.

6. The method of claim 1, wherein said one or more larger cells are cells from a blood sample.

7. The method of claim 1, wherein the distance between any given two obstacles comprised in said plurality of obstacles increases downstream from an inlet port adapted to receive said first fluid flow..

8. The method of claim 1, wherein said one or more smaller cells are from a blood sample.

9. The method of claim 1, wherein said plurality of obstacles are positioned at least partially across at least one of said first fluid flow and said second fluid flow.

10. The method of claim 1, wherein said plurality of obstacles differentially direct a subset of cells in said first fluid flow by contacting said subset of cells, wherein said subset of cells comprise less than all of the cells in said first fluid flow.

11. The method of claim 1, wherein adjacent obstacles in said plurality of obstacles comprise a gap therebetween sized to allow passage of said one or more smaller cells and deny passage of said one or more larger cells.

* * * * *